US009661875B2

(12) United States Patent
Karles et al.

(10) Patent No.: US 9,661,875 B2
(45) Date of Patent: *May 30, 2017

(54) METHODS AND COMPOSITIONS FOR PRODUCING HYDROGEL CAPSULES COATED FOR LOW PERMEABILITY AND PHYSICAL INTEGRITY

(71) Applicant: Philip Morris USA Inc., Richmond, VI (US)

(72) Inventors: Georgios D. Karles, Richmond, VI (US); Daqing Wu, Suwanee, GA (US); Shuzhong Zhuang, Richmond, VI (US)

(73) Assignee: Philip Morris USA Inc., Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/873,261

(22) Filed: Oct. 2, 2015

(65) Prior Publication Data

US 2016/0095347 A1 Apr. 7, 2016

Related U.S. Application Data

(62) Division of application No. 14/163,657, filed on Jan. 24, 2014, now Pat. No. 9,167,848, which is a division of application No. 12/612,881, filed on Nov. 5, 2009, now Pat. No. 8,663,671.

(51) Int. Cl.
| | |
|---|---|
| A24B 15/18 | (2006.01) |
| A23P 1/04 | (2006.01) |
| B01J 13/22 | (2006.01) |
| A24B 15/28 | (2006.01) |
| A24D 3/06 | (2006.01) |
| A61K 8/11 | (2006.01) |
| A61K 8/31 | (2006.01) |
| A61K 8/73 | (2006.01) |
| A61K 8/81 | (2006.01) |
| A61K 9/50 | (2006.01) |
| A61Q 19/00 | (2006.01) |
| C09B 67/02 | (2006.01) |
| A24B 13/00 | (2006.01) |
| A23P 10/30 | (2016.01) |
| A23L 27/00 | (2016.01) |

(52) U.S. Cl.
CPC ............ *A24B 15/186* (2013.01); *A23L 27/72* (2016.08); *A23P 10/30* (2016.08); *A24B 13/00* (2013.01); *A24B 15/283* (2013.01); *A24D 3/061* (2013.01); *A61K 8/11* (2013.01); *A61K 8/31* (2013.01); *A61K 8/731* (2013.01); *A61K 8/733* (2013.01); *A61K 8/8152* (2013.01); *A61K 9/5026* (2013.01); *A61K 9/5036* (2013.01); *A61K 9/5073* (2013.01); *A61Q 19/00* (2013.01); *B01J 13/22* (2013.01); *C09B 67/0097* (2013.01); *A23V 2002/00* (2013.01)

(58) Field of Classification Search
None
See application file for complete search history.

(56) References Cited

U.S. PATENT DOCUMENTS

| | | |
|---|---|---|
| 4,350,679 A | 9/1982 | Mizuno et al. |
| 4,715,143 A | 12/1987 | Redenbaugh et al. |
| 4,910,021 A | 3/1990 | Davis et al. |
| 4,967,772 A | 11/1990 | Waddell et al. |
| 5,016,655 A | 5/1991 | Waddell et al. |
| 5,096,717 A | 3/1992 | Wirth et al. |
| 5,330,759 A | 7/1994 | Pagay et al. |
| 5,843,479 A | 12/1998 | Kelm et al. |
| 6,197,331 B1 | 3/2001 | Lerner et al. |
| 6,312,728 B1 | 11/2001 | Beiman et al. |
| 6,365,189 B1 | 4/2002 | Quong |
| 6,780,507 B2* | 8/2004 | Toreki ............... A01N 25/006 264/4.1 |
| 6,858,666 B2 | 2/2005 | Hamer et al. |
| 6,923,988 B2 | 8/2005 | Patel et al. |
| 8,627,828 B2 | 1/2014 | Strickland et al. |
| 2005/0142199 A1 | 6/2005 | Tian et al. |
| 2005/0271724 A1 | 12/2005 | Clark et al. |
| 2006/0115529 A1 | 6/2006 | Jeong et al. |
| 2006/0144412 A1 | 7/2006 | Mishra et al. |
| 2006/0191548 A1* | 8/2006 | Strickland ............ A23L 1/2205 131/347 |
| 2007/0003619 A1 | 1/2007 | Smith |
| 2007/0003621 A1 | 1/2007 | Nangia et al. |
| 2007/0145617 A1 | 6/2007 | Finney et al. |
| 2007/0145618 A1 | 6/2007 | Finney et al. |
| 2008/0286408 A1 | 11/2008 | Karles et al. |
| 2010/0211158 A1* | 8/2010 | Haverty ............... B24C 1/10 623/1.15 |

FOREIGN PATENT DOCUMENTS

| | | |
|---|---|---|
| EP | 1607087 A1 | 12/2005 |
| JP | 2003/201256 A | 7/2003 |

(Continued)

OTHER PUBLICATIONS

International Search Report (Form PCT/ISA/210) and Written Opinion of the International Searching Authority (Form PCT/ISA/237) dated Jun. 20, 2011, issued by the European Patent Office in corresponding International Patent Application No. PCT/EP2010/006722.

(Continued)

*Primary Examiner* — H. Sarah Park
(74) *Attorney, Agent, or Firm* — Buchanan Ingersoll & Rooney PC

(57) ABSTRACT

Methods and compositions for producing hydrogel capsules enveloped with at least one coating layer is disclosed. The coating formulations deposited on the surface of the capsules can improve the physical integrity and the water-retention properties of the alginate beads. The coating formulations can be sequentially applied in various combinations to obtain desirable properties, such as improved physical integrity, mechanical strength, and low permeability, that can extend the shelf-life of the capsules when incorporated into various consumer products.

8 Claims, 14 Drawing Sheets

(56) References Cited

FOREIGN PATENT DOCUMENTS

| WO | WO 85/02972 A1 | 7/1985 |
| WO | WO 97/02020 A1 | 1/1997 |
| WO | WO 03/059503 A1 | 7/2003 |
| WO | WO 2004/041251 A1 | 5/2004 |
| WO | WO 2006/109194 A2 | 10/2006 |
| WO | WO 2007/002516 A2 | 1/2007 |

OTHER PUBLICATIONS

International Preliminary Report on Patentability issued May 8, 2012 for PCT/EP2011/006722.

* cited by examiner

FIG. 7A
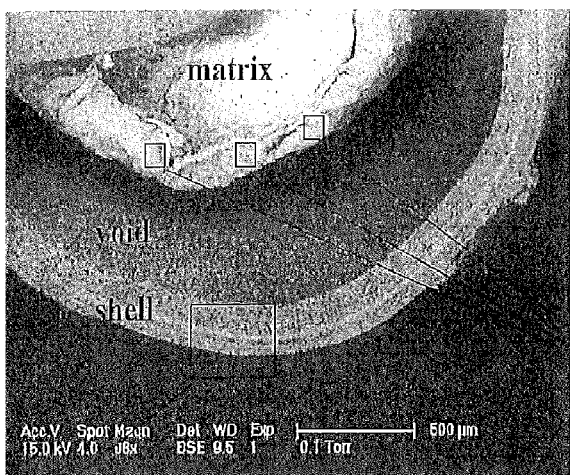
FIG. 7B
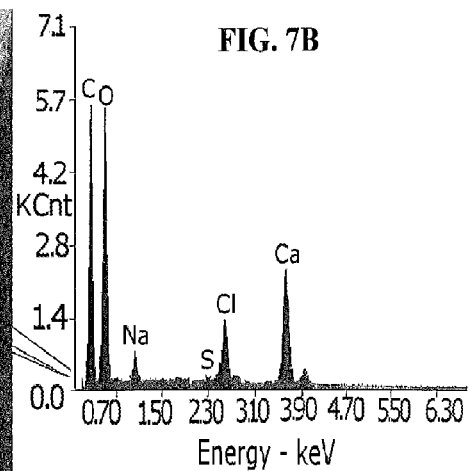
FIG. 7C
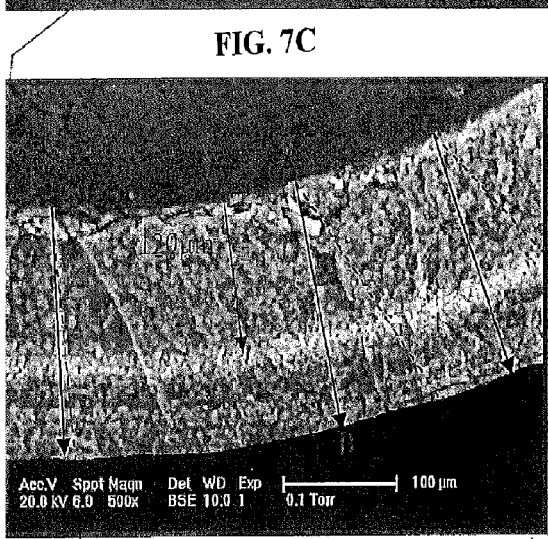
FIG. 7D
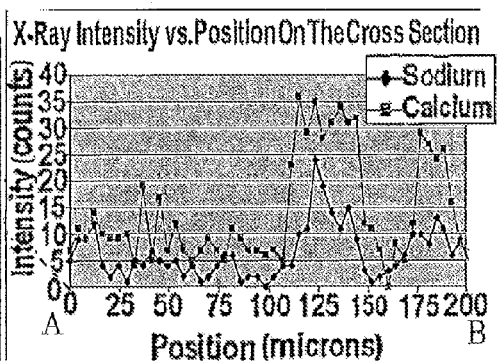
FIG. 7E
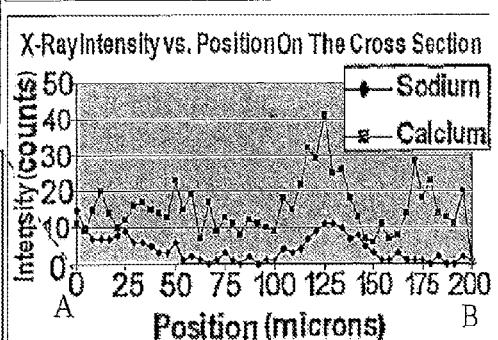
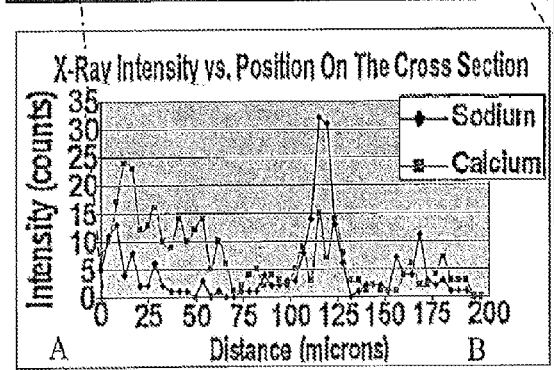
FIG. 7F

METHODS AND COMPOSITIONS FOR PRODUCING HYDROGEL CAPSULES COATED FOR LOW PERMEABILITY AND PHYSICAL INTEGRITY

CROSS-REFERENCE TO RELATED APPLICATION

This application is a divisional of U.S. application Ser. No. 14/163,657, filed on Jan. 24, 2014, which is a division of U.S. application Ser. No. 12/612,881, filed on Nov. 5, 2009, the entire content of each of which is incorporated herein by reference.

BACKGROUND

Hydrogels, formed as capsules, have been adapted as carrier devices for holding/delivering various molecules of interest that can be deposited within the core spaces of hydrogels. Typically, due to technical limitations, the molecules of interest were suspended in oil-based solvents resulting in a capsule structure comprising a hydrophobic core enclosed by a hydrophilic hydrogel matrix that can support substantial amounts of water (e.g., at least 70%). Such hydrogels comprising a hydrophobic core can be of limited use for many applications. The development of more advanced hydrogels comprising a hydrophilic core have been challenging because such capsules cannot maintain the phase separation between the hydrophilic core and the hydrophilic-hydrogel shell matrix, resulting in hydrogel capsules that exhibit sub-optimal properties, and therefore, are inadequate for long-term storage and/or prolonged usage.

SUMMARY

In various embodiments, methods and compositions for producing hydrogel capsules (for example, comprising alginate) enveloped with at least one coating layer are disclosed. Various embodiments are directed to tobacco-containing smokable and smokeless products comprising hydrogel capsules coated with at least one coating layer formulated as disclosed. Various embodiments are directed to tobacco-free consumer products comprising hydrogel capsules coated with at least one coating layer formulated as disclosed. The coating formulations deposited on the surface of hydrogel capsules can improve the physical integrity and the water-retention properties of the hydrogel capsules. The coating formulations can be sequentially applied in various combinations to obtain desirable properties, such as improved physical integrity, mechanical strength, and low permeability, that can extend the shelf-life of hydrogel capsules when incorporated into various consumer products.

BRIEF DESCRIPTION OF DRAWINGS

FIGS. 7A and 7C show a cross-sectional analysis of Eud-Alg hydrogel capsule as determined by environmental scanning electron microscopy ("ESEM"). FIG. 7B is an EDS spectrum of Eud-Alg hydrogel capsule. FIGS. 7D-7F show cross-sectional analysis of Eudragit® coating to determine Ca and Na content by x-ray line scans, as described in Example 3.

DETAILED DESCRIPTION

I. Definitions

Figure 1:
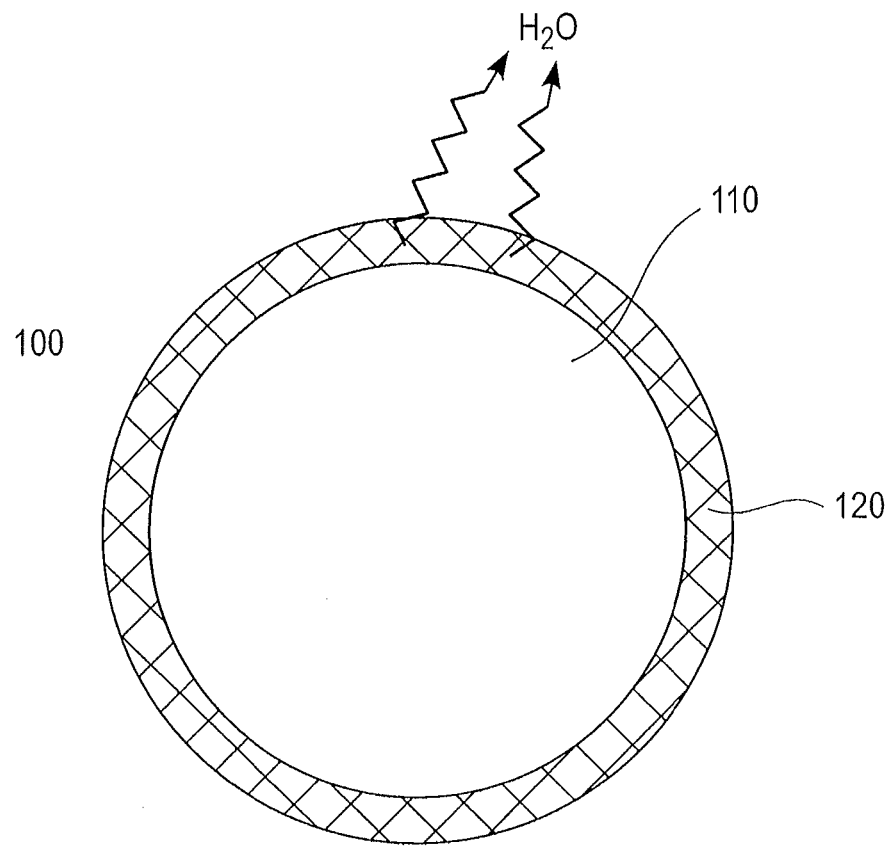
FIG. 1 is a schematic of a basic configuration of an hypothetical hydrogel capsule without a protective coating, which may be representative of similar structures disclosed in the prior art.

Throughout this disclosure and the appended claims, the terms "a" and "the" function as singular and plural referents unless the context clearly dictates otherwise. Thus, for example, a reference to "a core" includes a plurality of such cores, and a reference to "the hydrogel capsule" includes reference to one or more of such hydrogel capsules.

The term "hydrogel" refers to any network of polymer chains crosslinked together for stabilization, and is amenable to shaping into a desirable form (e.g., spherical, disk, elliptical, pod-like). Hydrogels include colloidal gels that can hold substantial amounts of water. Alginate is a preferred hydrogel. Other hydrogels include pectins and carrageenan.

As used herein, the term "about" when used in conjunction with a stated numerical value or range denotes somewhat more or somewhat less than the stated value or range, to within a range of ±10% of that stated.

The term "capsule" refers to a structure comprising at least one continuous surface of a material enclosed together to form at least one core in the interior space of the capsule. The terms capsule and bead are used interchangeably herein. In the simplest embodiment, the capsule comprises a single core, sufficient to carry a molecule of interest or a combination of molecules of interest.

The term "hydrophilic" refers to a charge-polarized molecule that, via hydrogen bonding, can associate more readily with water (or dissolve more readily in water) than with (or in) oil or other hydrophobic solvents. Hydrophilic molecules are typically positively or negatively charged, or zwitterionic, and include solute molecules and solvent molecules. Examples of hydrophilic molecules include water molecules, colloids, and any water-soluble molecules, such as alcohols.

The term "hydrophobic" refers to a neutrally-charged molecule, and includes non-polar solute molecules and non-polar solvent molecules. In water, hydrophobic molecules can cluster together to form micelles. Examples of hydrophobic molecules include alkanes, oils, and fats.

The terms "coating" or "coating layer" or "film" or "film layer" are interchangeably used. A coating layer may be deposited onto the surface of hydrogel capsules. A coating layer may be deposited onto the surface of another coating layer, in which case the "first" coating layer is applied before the "second" coating layer.

The term "tobacco" refers to any variety of the genus *Nicotiana*, and includes native tobacco variants, transgenic tobacco variants, and cultured tobacco grown in vitro. Exemplary species of tobacco include *N. rustica, N. tabacum* (e.g., LA B21, LN KY171, TI 1406, *Basma, Galpao, Perique, Beinhart* 1000-1, and *Petico*). Other species include *N. acaulis, N. acuminata, N. acuminata var. multiflora, N. africana, N. alata, N. amplexicaulis, N. arentsii, N. attenuata, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis subsp. hesperis, N. otophora, N. paniculata, N. pauciflora, N. petunioides, N. plumbaginifolia, N. quadrivalvis, N. raimondii, N. repanda, N. rosulata, N. rosulata subsp. ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N. x sanderae*. The tobacco may be whole, shredded, cut, cured, aged, fermented, or otherwise processed, e.g., granulated or encapsulated. Tobacco may also be in the form of finished products, including any non-combustible tobacco that can be orally consumed, e.g., smokeless tobacco and lit-end smokable products, such as cigars and cigarettes.

II. Formulations for Manufacturing Hydrogel Capsules

FIG. 1 is a schematic of a basic configuration of a hypothetical hydrogel capsule without a protective coating, which may be representative of similar structures disclosed in the prior art. In FIG. 1, the hydrogel capsule 100 comprises a core component ("core") 110 enclosed by a hydrogel matrix ("shell") 120. If molecules of interest are suspended in a hydrophobic solvent (e.g., oil) and deposited within the core 110 of the capsule, then the capsule is more likely to retain the initial physical integrity/shape defined at the time of manufacture due to inherent repulsive forces between the "hydrophobic" core and the "hydrophilic" shell. In contrast, if molecules of interest are suspended in a "hydrophilic" solvent (e.g., water) and deposited within the core 110 of the capsule, then the physical integrity/shape of the capsule is more likely to deviate substantially from the initial state (i.e., defined at the time of manufacture). After prolonged storage and/or prolonged use, the physical boundary between the hydrophilic core and the hydrophilic shell become less-defined. Furthermore, a hydrogel capsule comprising a hydrophilic core may be unsuitable to carry unstable molecules that are more likely to be inactivated (e.g., precipitation or aggregation of molecules of interest) if the concentration of these molecules increases due to water loss via evaporation. Thus, improvements in the manufacture of both types of hydrogel capsules are highly desirable.

The figures and examples herein provide: (1) exemplary formulations and methods for incorporating molecules of interest into the core of hydrogel capsules; (2) exemplary formulations and methods for manufacturing the hydrogel matrix/shell; and (3) exemplary formulations and methods for coating the hydrogel matrix/shell. Hydrogel capsules can be incorporated into various consumable products, including: (a) tobacco-containing products, such as (i) smoking tobacco products and (ii) smokeless tobacco products; and (b) consumable products without tobacco. Other uses include controlled release of active agents (such as nutraceuticals, water soluble flavors or drugs), cell immobilization, cell delivery, or cell storage. Coating formulations can be employed in the manufacture of: (a) hydrogel capsules comprising a hydrophilic core, and (b) hydrogel capsules comprising a hydrophobic core, although the examples may be described in the context of hydrogel capsules of type (a). The coating formulations can be sequentially applied in various combinations to obtain desirable properties. For example, the physical integrity, the mechanical strength, and the capacity for water retention of the capsules can be controlled. The improved shell/coating structure disclosed herein can overcome problems such as undesired swelling and dissolving of alginate capsules, thereby improving the shelf-life of the capsules, which is helpful for their incorporation into various consumer products.

Figure 2:
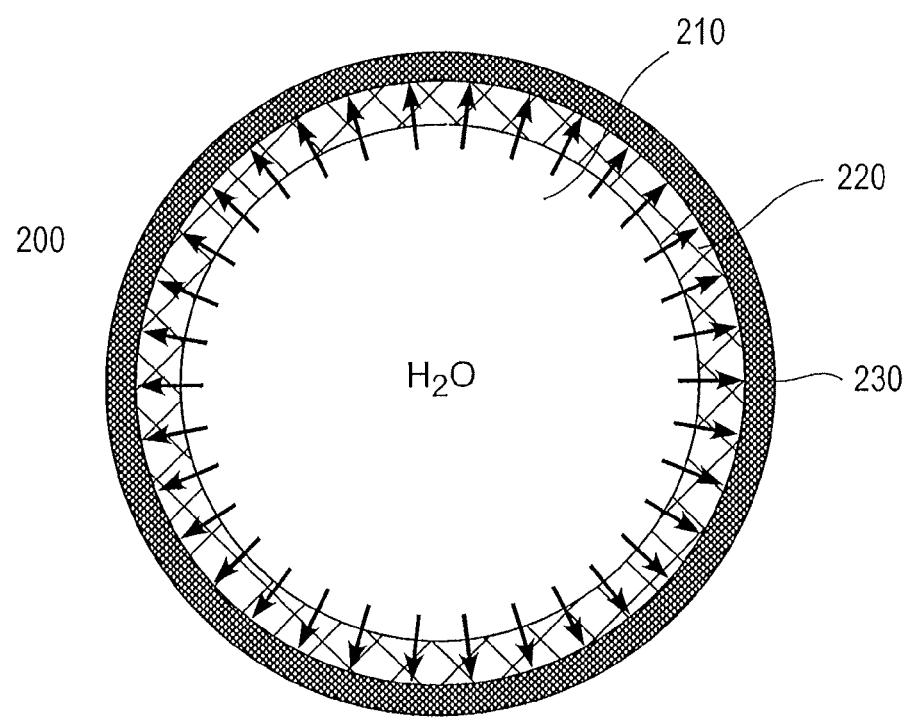
FIG. 2 is a schematic of a hydrogel capsule protected by at least one coating layer.

FIG. 2 is a schematic of a hydrogel capsule protected by at least one coating layer. In FIG. 2, an exemplary hydrogel capsule 200 is shown, comprising: a core 210, a hydrogel matrix/shell 220, and one coating layer 230 that envelops the exterior surface of the hydrogel matrix/shell 220. The coating layer 230 can serve as a protective layer or a protective film to maintain in or to strengthen the physical integrity of the hydrogel capsule. The coating layer 230 can reduce the permeability of the hydrogel capsule by serving as a physical barrier that can prevent the diffusion of water molecules from the exterior surface of the hydrogel matrix/shell 220. If the hydrogel capsule comprises a hydrophilic core, then water molecules from the hydrophilic core 210 will tend to diffuse into the hydrogel matrix/shell 220 to replace the water molecules that have evaporated from the surface of the hydrogel matrix/shell 220, which would result in shrinkage of the hydrogel capsule 200. If the coating layer 230 deposited on the surface of the hydrogel shell 220 is not effective, shrinkage of the hydrogel capsule 200 may occur, and cracks and other deformation of the coating layer 230 may result. FIGS. 6A, 8A, 8C, 13A, and 13B illustrate the effectiveness of depositing Eudragit® as a coating layer for protecting alginate hydrogel capsules as determined by optical imaging or surface morphology analysis.

A. Exemplary Core Additives

Various molecules of interest can be included as additive components of the core within the hydrogel capsules, including various flavor agents, sensates, sequestering agents, coloring agents, plasticizing agents, complexing agents, filling agents, natural and/or artificial sweeteners, binders, thickening agents, souring agents, pigments, surfactants, stabilizing agents, antioxidants, preservatives, humectants, medicaments, tobacco, tobacco extracts, equivalents, and other additives as described below.

The term "controlled-release" refers to the capacity to control the release profile of an encapsulation device, such as hydrogel capsules described herein. Any of these components can be encapsulated individually, or as a combination, into smaller capsules in order to control the release profile for any component as desired. For example, if a fast-release profile is desired for a first flavorant of interest, then the porosity of the polymer constituting the capsules can be increased. In contrast, if a slow-release profile is desired for a second flavorant of interest, then the porosity of the polymer constituting the capsules can be decreased.

1. Flavorants and Sensates

Suitable flavorants, which may generate taste and/or aroma, include any natural or synthetic flavorant, such as tobacco, smoke, menthol, mint, such as peppermint and spearmint, chocolate, licorice, citrus and other fruit flavorants, gamma octalactone, vanillin, ethyl vanillin, breath freshener flavorants, spice flavorants such as cinnamon, methyl salicylate, linalool, bergamot oil, geranium oil, lemon oil, and ginger oil. Other suitable flavorants may include flavorant compounds selected from the group consisting of an acid, an alcohol, an ester, an aldehyde, a ketone, a pyrazine, combinations thereof and equivalents. Suitable flavorant compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-valeric acid, combinations thereof and equivalents. In addition, flavorants can also be encapsulated for controlled delivery. Exemplary additional natural and artificial flavorants include peppermint, spearmint, wintergreen, menthol, cinnamon, chocolate, vanillin, licorice, clove, anise, sandalwood, geranium, rose oil, vanilla, lemon oil, cassia, spearmint, fennel, ginger, ethylacetate, isoamylacetate, propylisobutyrate, isobutylbutyrate, ethylbutyrate, ethylvalerate, benzylformate, limonene, cymene, pinene, linalool, geraniol, citronellol, citral, peppermint oil, orange oil, coriander oil, borneol, fruit extract, and equivalents. In a preferred embodiment, flavorant agents include essential oils and essences of coffee, tea, cacao, and mint. A suitable amount of a flavorant present in the core ranges from about 0.001 wt % to about 50 wt %. In a preferred embodiment, the amount ranges from about 1 wt % to about 40 wt %. In a preferred embodiment, the amount ranges from about 10 wt % to about 30 wt %. The flavorant may be incorporated as a solid powder, sprayed dried as a liquid, or mixed with starch or gum-type matrix.

Sensates are ingredients that can induce a sensorial experience, such as tingling, sensation of warmth, sensation of cooling, and equivalents. Suitable sensates include sensate agents such as acetic acid, adipic acid, citric acid, lactic acid, maleic acid, succinic acid, tartaric acid, equivalents and mixtures thereof. A suitable amount of a sensate agent ranges from about 0.001 wt % to about 5 wt %. In a preferred embodiment, the amount of sensate agent ranges from about 0.1 wt % to about 2 wt %.

2. Sequestering Agents

For embodiments wherein the alginate capsules include tobacco, sequestering agents can be employed for binding components of tobacco or tobacco extracts, such as tobacco-specific nitrosamines ("TSNAs") within the core of the hydrogel capsule. Sequestering agents can be effective in reducing the diffusion or transport of certain TSNAs from various tobacco-containing products (e.g., pouched products) into a consumer's mouth. Suitable sequestering agents include polyvinylpolypyrrolidone. A suitable amount of sequestering agent ranges from 0.001 up to about 5 wt %, and more preferably ranges up to about 2 wt %.

3. Antioxidants and Preservatives

The capsules can optionally include antioxidants and/or preservatives. Exemplary antioxidants include ascorbic acid, vitamin E, and sodium pyrosulfate. Exemplary preservatives include acetic acid, benzoic acid, citric acid, lactic acid, malic acid, sorbic acid, and tartaric acid. A suitable amount of an antioxidant and/or preservative ranges from 0.001 up to about 5 wt %, and more preferably ranges up to about 2 wt %.

4. Tobacco/Tobacco Extracts and Tobacco Capsules

In an embodiment, the capsules can include a tobacco component. Any raw or processed forms of tobacco, e.g., as a powder/dust, a granule, a shred, a slurry, a flowable gel, and equivalents can be added to the capsules. The final tobacco concentration in the capsules ranges from 1 percent to 99 percent by weight of the final composition, for example, and ranges at most from about 10%, 15%, 20%, 25%, 30%, 35%, 40%, 45%, 50%, 55%, 60%, 65%, 70%, 75%, 80%, 85%, or 90% tobacco. In an embodiment, the alginate capsules include about 20 to 30% tobacco.

Humectants can be employed for maintaining and protecting the moisture levels of the tobacco material in tobacco-containing hydrogel capsules. Humectants can be employed as preservatives to remove excess water and thereby, reduce the growth of micro-organisms. Humectants can be employed for providing a higher moisture feel in a drier tobacco material (or tobacco substitute material) or a drier smokeless tobacco material. Examples of humectants include glycerol and propylene glycol. A suitable amount of a humectant ranges from about 0.001 wt % to about 5 wt %. More preferably, the amount ranges from about 0.1 wt % to about 2 wt %.

Exemplary binders include mono based or polysaccharide based materials, modified cellulosics, starches, and/or cellulose ethers. A suitable amount of a binder ranges from 0.001 up to about 20 wt %, and more preferably the amount ranges up to about 10 wt %. Exemplary thickening agent include polymers such as polyvinyl pyrrolidone and polyvinyl alcohol, and gums such as xanthan gum, gum arabic, and acacia gum. Generally, the stiffness of capsules can be increased and the dissolution rate (i.e., dissolution upon exposure to moisture) can be decreased by increasing the average molecular weight of polymers that form a film. Thickening agents can be added to the core of the capsules to increase the modulus (i.e., stiffness) of the capsules and to reduce the deformation of capsules during/after the drying step (e.g., during storage). A suitable thickening agent ranges from 0.001 up to about 20 wt. %, and more preferably ranges from 0.001 up to about 5 wt. % of the final dried composition.

5. Other Components

The capsules can optionally contain medicaments, nutraceuticals, and/or cosmetics. Examples thereof include vitamins, perfumes, and ointments.

The capsules can optionally contain products not intended for human consumption, for example agrochemicals, disinfectants, detergents, and dyestuff.

Filling agents can be employed for controlling the physical properties of the hydrogel capsule (e.g., texture, weight, etc.). Exemplary filling agents include cellulose, titanium oxide, magnesium silicate (e.g., talc), aluminum silicate, magnesium carbonate, calcium carbonate (e.g., limestone), calcium phosphate, calcium sulfate, zinc oxide, aluminum oxide, equivalents, equivalents, and mixtures thereof. Filling agents such as carbonate and phosphate salts can also be used to adjust the pH. In a preferred embodiment, the pH of the capsules is greater than 5, more preferably greater than 6 (e.g., greater than 6.5, 7, or 7.5). The filling agents can be incorporated in an amount up to about 50 wt. %.

Suitable natural and/or artificial sweeteners include water soluble sweeteners such as monosaccharides, disaccharides, and polysaccharides (e.g., xylose, ribose, sucrose, maltose, fructose, glucose, maltose, mannose). A suitable amount of a sweetener ranges from about 0.001 wt % to about 5 wt %. In a preferred embodiment, the amount of a sweetener ranges from about 0.1 wt % to about 2 wt %.

Plasticizing agents can be employed for controlling the stiffness and the viscosity of a polymer melt during casting or extrusion. Exemplary plasticizing agents include monoacetin; diacetin; triacetin; glycols such as polyethylene glycol and propylene glycol; polyhydric alcohols such as glycerin and sorbitol; mineral oils; vegetable oils; glycerol and glycerol esters such as glycerol triacetate. A suitable amount of a plasticizing agent ranges from 0.001 up to about 20 wt. %, and more preferably ranges up to about 5 wt. %.

Exemplary stabilizing agents include various gums such as guar gum, xanthan gum, locust bean gum, and carrageenan. A suitable amount of a stabilizing agent ranges from 0.001 up to 10 wt. %, and more preferably ranges up to about 2 wt. % of the final composition.

Suitable surfactants include mono and diglycerides of fatty acids, lactylates, pluronic acid, polyoxyethylene sorbitol esters, latanol, sodium lauryl sulfate, and equivalents. A suitable amount of surfactants ranges from 0.001 up to about 10 wt. %, and more preferably ranges up to about 2 wt. % of the final composition.

Suitable pigments or coloring agents can be incorporated in an amount from 0.001 up to about 5 wt. % of the final composition.

B. Production of Hydrogel Matrix/Shell

For manufacturing hydrogel matrix/shell, suitable crosslinkable polymers include alginates, pectins, carrageenan, and equivalents thereof. An exemplary formulation for producing an alginate hydrogel is provided in Example 1. The various components suitable for incorporation into the core component can be suitable for incorporation into the hydrogel matrix/shell (e.g., flavorants, pigments).

A crosslinked polymer can be obtained by various methods, including by ionic gelation, in which ions are added to a suspension of the monomers of a suitable polymer. Examples of ions suitable to activate ionic gelation include, sodium, potassium, calcium, aluminum, lanthanum, magnesium, and barium. A suitable amount of a polymer ranges in an amount up to about 95 wt %, more preferably from about 0.5 wt % to about 85 wt %, and most preferably from about 10 wt % to about 75 wt % based on the total weight of hydrogel matrix/shell. The rate of diffusion of components contained in the core can be controlled by adjusting the thickness and/or porosity of the matrix/shell. For example, if alginate hydrogel capsules are manufactured, then the porosity of matrix/shell (i.e., crosslinking density) can be controlled by adjusting the ratio of mannuronic units to guluronic units (M:G) to form the alginate polymer. For example, to obtain a fluid-like consistency, the mannuronic: guluronic ratio should be greater than 1:1, and the ratio may range from about 1.5-3:1. In contrast, to obtain a gel-like consistency, the mannuronic:guluronic ratio should be less than 1:1, and the ratio may range from about 0.4:1-0.6:1.

C. Exemplary Coating Formulations and Coating Configurations

Figure 3A:
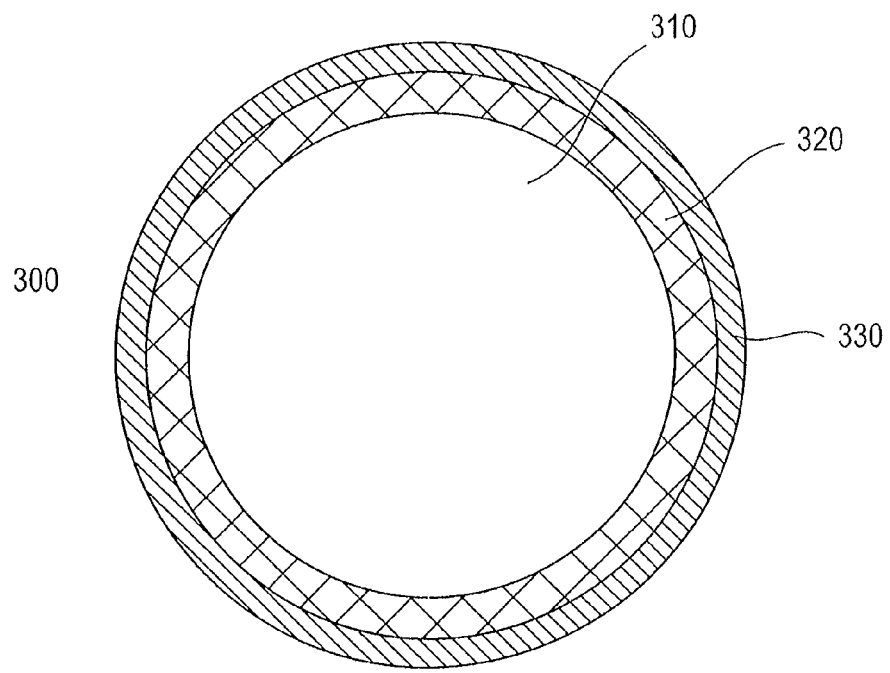
FIG. 3A is a schematic of a hydrogel capsule protected by at least one coating layer comprising a film-forming material.
Figure 3B:
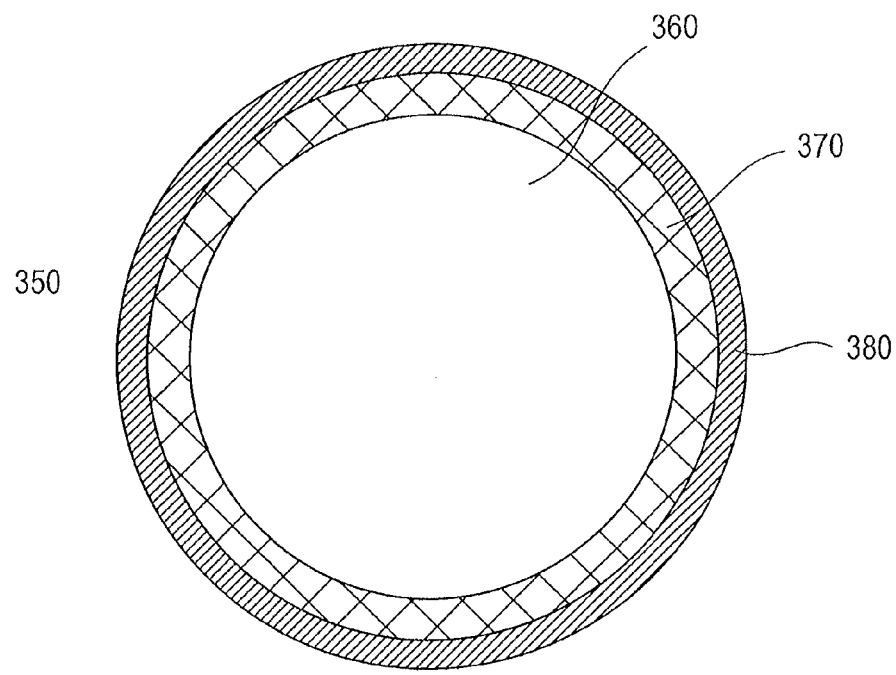
FIG. 3B is a schematic of a hydrogel capsule protected by at least one coating layer comprising a wax.
Figure 4:
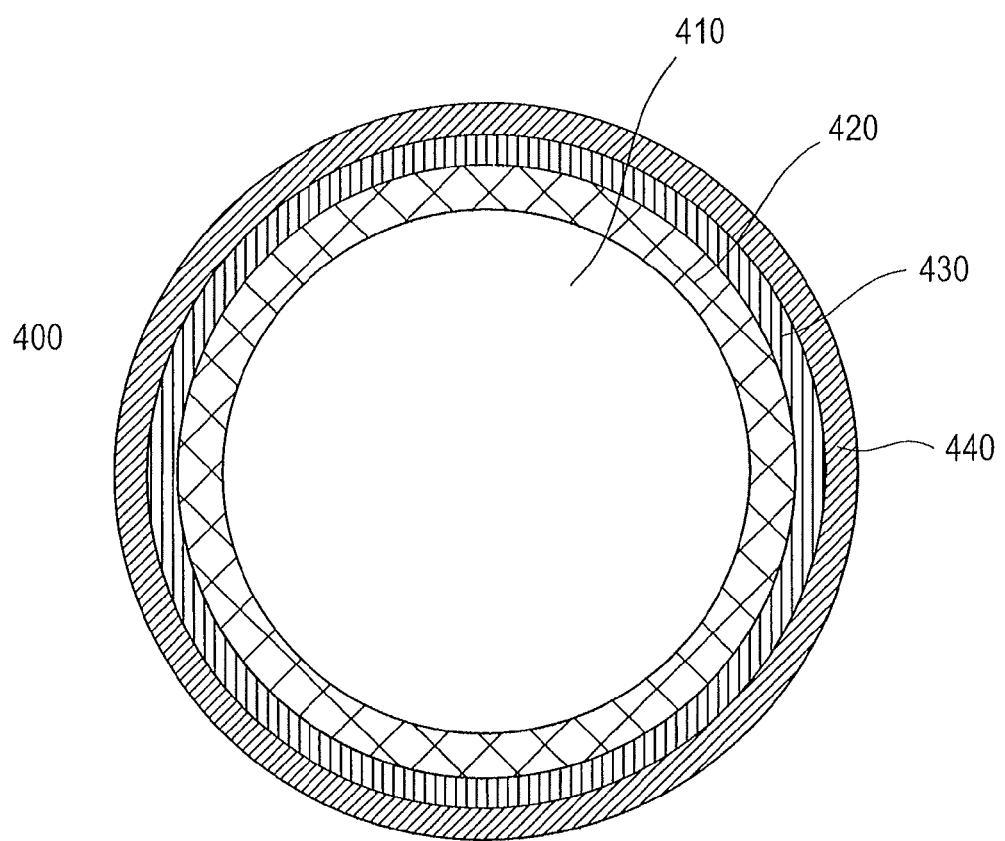
FIG. 4 is a schematic of a hydrogel capsule protected by at least two coating layers.

In the following, FIGS. 3A, 3B, and 4 provide exemplary coating configurations that have been described further in Examples 1-10. The various components suitable for incorporation into the core component can be suitable for incorporation into a coating layer (e.g., flavorants, pigments, souring agents).

FIG. 3A is a schematic of a hydrogel capsule protected by at least one coating layer comprising a film-forming material. In FIG. 3A, an exemplary hydrogel capsule 300 is shown, comprising: a core 310 comprising one or more components as described herein, a hydrogel matrix/shell 320 of one or more polymer materials as described herein, and one coating layer 330 of one or more coating materials as described herein that envelops the exterior surface of the hydrogel matrix/shell 320. In an embodiment, a hydrogel capsule comprises: a core; a hydrogel matrix/shell; and a coating layer such as a film-forming latex that completely envelops the exterior surface of the hydrogel matrix/shell.

As another example, a hydrogel capsule may comprise: a core that includes at least one core component such as a flavorant and/or sensate; a hydrogel matrix/shell; and a coating layer comprising a film-forming latex that completely envelops the exterior surface of the hydrogel matrix/shell.

According to one embodiment, a tobacco-containing hydrogel capsule comprises: a core that includes tobacco and/or tobacco extract; a hydrogel matrix/shell selected from the group consisting of alginates, pectins, and carrageenan; and a single coating layer selected from the group consisting of Eudragit® L30D-55 and (acrylamidomethyl)cellulose acetate propionate (ACAP). Various embodiments are directed to a tobacco-containing hydrogel capsule, comprising: a core that includes tobacco, tobacco extract, and/or a sequestration agent; a hydrogel matrix/shell selected from the group consisting of alginates, pectins, and carrageenan; and a single coating layer selected from the group consisting of Eudragit® L30D-55 and (acrylamidomethyl)cellulose acetate propionate (ACAP).

FIG. 3B is a schematic of a hydrogel capsule protected by at least one coating layer comprising a wax. In FIG. 3B, an exemplary hydrogel capsule 350 is shown, comprising: a core 360 comprising one or more components as described herein, a hydrogel matrix/shell 370 of one or more polymer materials as described herein, and a single coating layer 380 of one or more coating materials as described herein that envelops the exterior surface of the hydrogel matrix/shell 370. In various embodiments, a hydrogel capsule comprises: a core; a hydrogel matrix/shell; and a single coating layer comprising a wax that completely envelops the exterior surface of the hydrogel matrix/shell. In various embodiments, a hydrogel capsule comprises: a core that includes at least one flavorant and/or sensate; a hydrogel matrix/shell; and a single coating layer comprising a wax that completely envelops the exterior surface of the hydrogel matrix/shell.

According to one embodiment, a tobacco-containing hydrogel capsule comprises: a core that includes tobacco and/or tobacco extract; a hydrogel matrix/shell selected from the group consisting of alginates, pectins, and carrageenan; and a single coating layer selected from the group consisting of paraffin wax, carnauba wax, and polyester wax. Various embodiments are directed to a tobacco-containing hydrogel capsule, comprising: a core that includes tobacco, tobacco extract, and/or a sequestration agent; a hydrogel matrix/shell selected from the group consisting of alginates, pectins, and carrageenan; and a single coating layer selected from the group consisting of paraffin wax, carnauba wax, and polyester wax.

FIG. 4 is a schematic of a hydrogel capsule protected by at least two coating layers. In FIG. 4, an exemplary hydrogel capsule 400 is shown, comprising: a core 410 comprising one or more components as described herein, a hydrogel matrix/shell 420 of one or more polymer materials as described herein, a first coating layer 430 of one or more coating materials as described herein that envelops the exterior surface of the hydrogel matrix/shell 420, and a second coating layer 440 of one or more coating materials as described herein that envelops the exterior surface of the hydrogel matrix/shell 430.

Various embodiments are directed to a hydrogel capsule, comprising: a core; a hydrogel matrix/shell; a first coating layer comprising a first film-forming material that envelops the exterior surface of the hydrogel matrix/shell; and a second coating layer comprising a second film-forming material that envelops the exterior surface of the first coating layer. Various embodiments are directed to a hydrogel capsule, comprising: a core that includes at least one flavorant and/or sensate; a hydrogel matrix/shell such as alginate, pectin and/or carrageenan; a first coating layer comprising a first film-forming material that envelops the exterior surface of the hydrogel matrix/shell; and a second coating layer comprising a second film-forming material such as a wax or latex film that envelops the exterior surface of the first coating layer.

According to one embodiment, a hydrogel capsule comprises: a core; a hydrogel matrix/shell selected from the group consisting of alginates, pectins, and carrageenan; a first coating layer comprising a first film-forming material that envelops the exterior surface of the hydrogel matrix/shell; and a second coating layer selected from the group consisting of paraffin wax, carnauba wax, and polyester wax.

According to another embodiment, a tobacco-containing hydrogel capsule comprises: a hydrogel capsule comprising: a core that includes tobacco and/or tobacco extract and optionally a sequestration agent, flavorant and/or sensate; a hydrogel matrix/shell; a first coating layer comprising a film-forming material that envelops the exterior surface of the hydrogel matrix/shell; and a second coating layer comprising a wax that envelops the exterior surface of the first coating layer.

III. Smokeless Tobacco Products

Various embodiments are directed to smokeless tobacco products, comprising at least one hydrogel capsule as described throughout this disclosure. Examples of smokeless tobacco products include snuff (moist or dry), chewing tobacco, loose tobacco, pouched tobacco, and equivalents. The disclosed smokeless tobacco products have a number of advantages, including longer shelf-life, improved taste, improved sensorial experience, and prolonged enjoyment in the use of such products due to the encapsulation of tobacco and other components. Tobacco and tobacco extracts can be interchangeably utilized.

The size, shape, and configuration of hydrogel capsules that can be incorporated into various smokeless pouched tobacco products can vary substantially. The following FIGS. 5A-5D provide examples of such products.

Figure 5A:
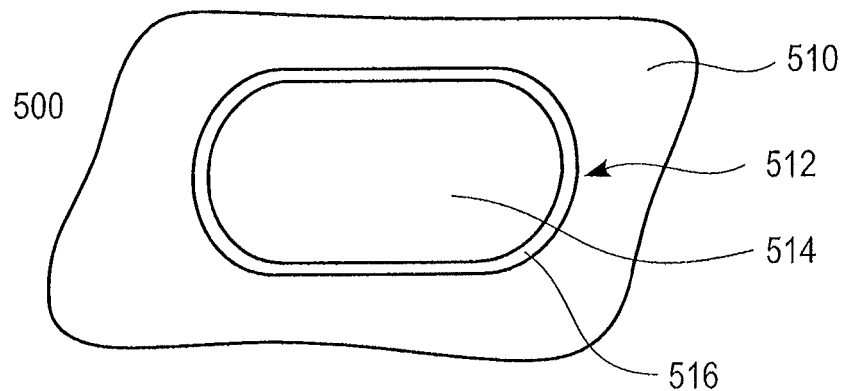
FIG. 5A is a schematic of a pouched tobacco product comprising a single hydrogel capsule protected by at least one coating layer.

FIG. 5A is a schematic of a pouched tobacco product comprising a single hydrogel capsule protected by at least one coating layer. In FIG. 5A, the pouch product 500 comprises: a porous membrane 510 that encloses a single hydrogel capsule 512 comprising a hydrogel matrix/shell 516 that encloses a core 514 that includes a tobacco material, a flavorant, a sensate, and/or a sequestration agent. Alternatively, the tobacco material can be further encapsulated.

Figure 5B:
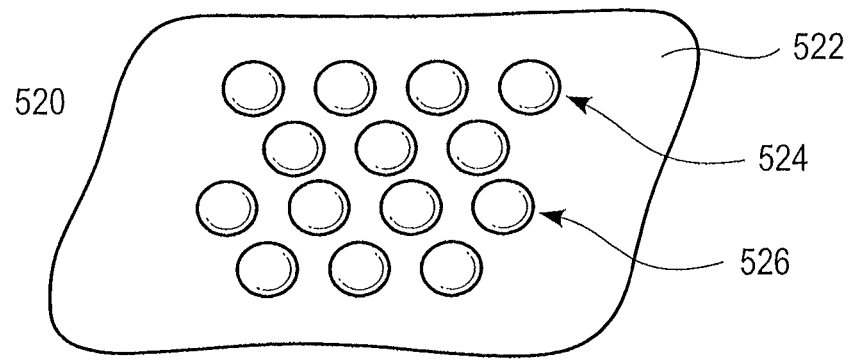
FIG. 5B is a schematic of a pouched tobacco product comprising multiple hydrogel capsules, each protected by at least one coating layer.

FIG. 5B is a schematic of a pouched tobacco product comprising multiple hydrogel capsules, each protected by at least one coating layer. In FIG. 5B, the pouch product 520 comprises: a porous membrane 522 that encloses multiple hydrogel capsules, such as 524 and 526, wherein each hydrogel capsule comprising a hydrogel matrix/shell that encloses a core that includes a tobacco material, a flavorant, a sensate, and/or a sequestration agent.

IV. Smokable Tobacco Products

Various embodiments are directed to smokable tobacco products, comprising at least one hydrogel capsule as described throughout this disclosure. The disclosed smokable tobacco products have a number of advantages, including longer shelf-life, improved taste, improved sensorial experience, and prolonged enjoyment in the use of such products due to the encapsulation of tobacco and other components. Tobacco and/or tobacco extracts can be utilized.

The hydrogel capsules can be incorporated into the filters of various smoking products, such as cigars and cigarettes. The smoking articles have a longer shelf-life because the volatile flavors and sensates can be stabilized within the core of the capsules, due to at least one coating later that reduces the permeability of the hydrogel capsule. During smoking, the essence of tobacco, flavorants, and sensates can be released at different time points and prolong the enjoyment of the smoking article. The composition of the hydrogel matrix can be modified in order to obtain a desirable flavorant-release profile.

V. Consumer Products without Tobacco:

Various embodiments are directed to tobacco-free consumer products comprising at least one hydrogel capsule as described throughout this disclosure.

EXAMPLES

Example 1

Preparation of Calcium Alginate Hydrogel Capsules and Exemplary Coating Formulations Alginate hydrogel capsules impregnated with water molecules can be formed by cross-linking together alginate polymer chains in a reaction mediated by $Ca^{2+}$ ions that can enter the electronegative, inter-chain cavities of the alginate polysaccharide promoting the formation of rod-like, cross-linked matrix structure. As an example, 4-5 mm diameter alginate hydrogel capsules were formed by reacting together 2% sodium alginate aqueous solution at pH 7.7 and 5% $CaCl_2$ solution at pH 7.0. A transfer pipette (with an opening of approximately 4 mm in diameter) was used to dispense 25 ml of 2% sodium alginate aqueous solution as droplets into 30 ml of 5% $CaCl_2$ solution. The mixture was stirred using a magnetic stirrer at 260 rpm for 30 seconds to form water-impregnated alginate hydrogel capsules (Alg) with a diameter of approximately 4 mm. The hydrogel capsules were then transferred into 200 ml of distilled water and stirred using a magnetic stirrer at 260 rpm for 3 min to stop the alginate cross-linking reaction with the calcium ions. These cross-linked hydrogel capsules contained approximately 97% water content by weight, and exhibited sufficient structural integrity to be subjected to subsequent coating steps with various polymers and/or wax, as described below.

To form hydrogel capsules protected with two coating layers, each coating layer was sequentially deposited over alginate hydrogel capsules according to the following procedure. Ten alginate hydrogel capsules were placed into 10 ml of a 30% aqueous dispersion of Eudragit® ("Eud") and were shaken gently for 30 seconds. The Eud-coated alginate hydrogel capsules ("Eud-Alg") were then physically separated from the aqueous medium using a sieve. A second coating was obtained by immersing Eud-Alg hydrogel capsules into a 12% ACAP solution (12% ACAP-Eud-Alg hydrogel capsules), or a 24% ACAP solution (24% ACAP-Eud-Alg hydrogel capsules), in acetone with castor oil (3% w/v), respectively, for 10 seconds. These double-coated hydrogel capsules ("ACAP-Eud-Alg") were then separated from the solution using a sieve. Both of these concentrations produced workable viscosities. Castor oil (3% w/v) was added to each solution to prevent the hydrogel capsules from adhering to each other. Acetone may be employed for facilitate the rate of evaporation during ACAP layer formation at room temperature.

Alternatively, to form hydrogel capsules protected with two coating layers, in which one coating layer comprises a wax formulation: 1) Eud-Alg hydrogel capsules were placed in a dry-ice-acetone bath for 1 min; 2) the frozen Eud-Alg hydrogel capsules were placed into molten wax and were shaken for 5 seconds; and 3) the wax-coated hydrogel capsules ("Wax-Eud-Alg") were collected on filter paper and cooled to room temperature.

Materials used in the examples include: alginic acid sodium salt (Alg) from brown algae, with the viscosity of a 2% solution at 25° C. being ~250 cps; (acrylamidomethyl) cellulose acetate propionate (ACAP), average $M_n$ ~20,000 by GPC; carnauba wax, refined, No.1 yellow (melting point 83° C. to 86° C.); granular paraffin waxes (melting points ranging from 48° C. to 74° C.) available from Sigma-Aldrich (Sigma-Aldrich Corporation, St. Louis, Mo. 63103 USA); Eudragit® L30D-55 (Eud), Mw approx. 250,000, a methacrylic acid, and ethyl acrylate copolymer dispersion with 30% solids available from Degussa (Röhm America, Piscataway, N.J., USA); and polyester wax available from VWR International Ltd. 1310 Goshen Parkway, West Chester, Pa. 19380, USA.

Example 2

Images of Alginate Hydrogel Capsule Coated with Eudragit® L30D-55

Figure 6A:
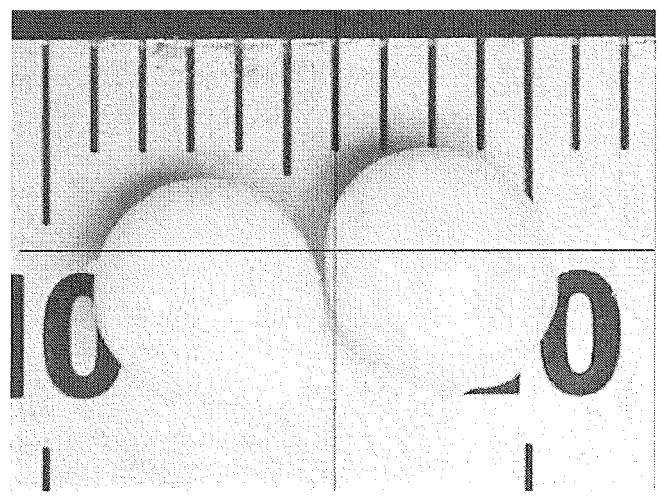
FIG. 6A is an image of an exemplary alginate (Alg) hydrogel capsule coated with Eudragit® L30D-55 (a methacrylic acid-co-ethyl acrylate latex referred to herein as "Eud") to form Eud-Alg hydrogel.
Figure 6B:
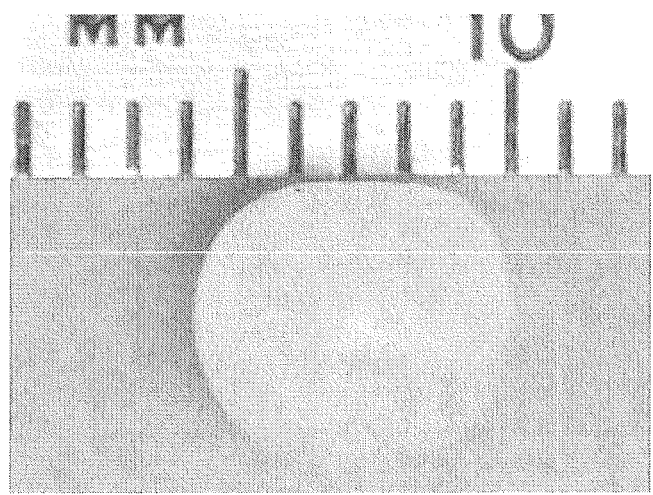
FIG. 6B is an image of an exemplary hydrogel capsule, first coated with Eudragit® L30D-55, and coated subsequently with a wax formulation to form Wax-Eud-Alg hydrogel, as described in Example 2.

FIG. 6A is an image of an exemplary alginate hydrogel capsule coated with Eudragit® L30D-55 to form Eud-Alg hydrogel. FIG. 6B is an image of an exemplary hydrogel capsule, which is first coated with Eudragit® L30D-55, and coated subsequently with a wax formulation to form Wax-Eud-Alg hydrogel. Each image contains a scale showing distance in mm. Eudragit® L30D-55 was deposited onto the surface of alginate hydrogel capsules by immersing freshly prepared alginate hydrogel capsules into an aqueous dispersion of Eudragit® at a pH of 2.5-3.5. Under visual examination, the surface of these Eud-Alg hydrogel capsules appeared smooth and uniform. Although the principles governing the interaction between the Eudragit®-dispersed phase and the alginate hydrogel capsules have not been fully characterized, it is conceivable that, when these hydrogel capsules are immersed in an acidic dispersion of Eudragit®, the negatively charged carboxylate ions of Eudragit® can interact with the $Ca^{2+}$ present on the surface of alginate hydrogel capsules, leading to coating formation. The thickness of Eudragit® coating layer can be controlled by adjusting the duration of the reaction and the percentage of Eudragit® included in the aqueous dispersion.

Example 3

Characterization of Eudragit®-Alginate Hydrogel Capsules

FIGS. 7A and 7C show a cross-sectional analysis of Eud-Alg hydrogel capsule as determined by ESEM. In FIG. 7A, both the core of the alginate hydrogel matrix and the Eudragit® coating layer demonstrated shrinkage after exposure to a vacuum during sample preparation for ESEM analysis, generating an artifactual void between the alginate hydrogel matrix shell and the Eudragit® coating layer. The Eudragit® coating layer demonstrated significant mechanical integrity by not collapsing or fracturing in response to the shrinkage of alginate core. In FIG. 7C, the cross-sectional thickness of Eudragit® coating layer was determined to be about 200 μm. The Eudragit® coating layer also contained Na and Ca, and a band rich in Na and Ca appeared to be present about 125 μm from the interior surface of the Eudragit® coating layer (arrow).

FIG. 7B is an energy dispersive spectrum ("EDS") of an Eud-Alg hydrogel capsule. In FIG. 7B, the alginate contained a significant amount of Ca and less substantial amount of Na, suggesting that Ca on the surface of alginate hydrogel capsules migrated into the Eudragit® coating layer during the coating process.

FIGS. 7D-7F show cross-sectional analysis of Eudragit® coating to determine Ca and Na content by x-ray line scans.

The cross-sectional thickness of the Eudragit® coating layer was determined by cross cutting the Eud-Alg hydrogel capsules with a razor blade. The cross cut hemispheres were then placed with the cut face up, onto a 25.4 mm diameter carbon adhesive disk attached to a 32 mm diameter aluminum stub. Cross sections were imaged using an FEI XL30 Environmental Scanning Electron Microscope (ESEM) operating at 15 to 20 kV in $H_2O$ vapor mode at a pressure of 0.1 to 1.1 torr. Selected area elemental analyses were performed on the uncoated cross sections using the EDAX energy dispersive spectrometer (EDS) interfaced with the EDAX Genesis software. X-ray line scans were also generated over the freshly-cut cross sections on the copolymer shells.

Example 4

Surface Morphology of Eudragit®-coated Alginate Hydrogels

Figure 8A:
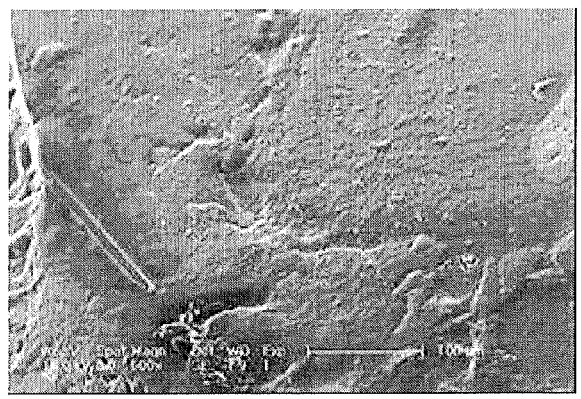
FIG. 8A shows the surface morphology of an exemplary Eud-Alg hydrogel capsule, as described in Example 4.

FIG. 8A shows the surface morphology of Eud-Alg hydrogel capsules. In FIG. 8A, the surface of the Eudragit® coating layer appeared to be rough and textured displaying random arrays of submicron pores, less than 3 μm throughout the samples. Some surface particles appeared to blend into the surface of the Eudragit® coating layer.

Figure 8B:
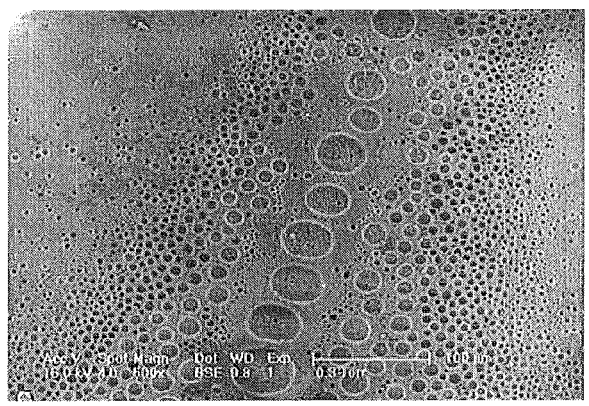
FIG. 8B shows the surface morphology of an exemplary 12% ACAP-Eud-Alg hydrogel capsule, in which "ACAP" represents (acrylamidomethyl)cellulose acetate propionate, as described in Example 4.

FIG. 8B shows the surface morphology of 12% ACAP-Eud-Alg hydrogel capsules, in which "ACAP" represents (acrylamidomethyl)cellulose acetate propionate. In FIG. 8B, the surface of the ACAP coating layer contained an array of circular indentations, or pits. These surface phenomena may have been formed by the fast rate of acetone evaporation from the ACAP coating layer at room temperature.

Figure 8C:
FIG. 8C shows the surface morphology of an exemplary Eud-Alg hydrogel capsule exposed to 120° C. for 5 min, as described in Example 4.

FIG. 8C shows the surface morphology of thermally treated Eud-Alg hydrogel capsules exposed to 120° C. for 5 min. In FIG. 8C, the surface of the Eud-Alg hydrogel capsules appeared to be smoother after exposure to 120° C. for 5 min, when compared to the surface appearance of 12% ACAP-Eud-Alg hydrogel capsules as shown in FIG. 8B.

Surface morphological characterization was facilitated by placing the samples onto 12 mm diameter carbon adhesive disks that were attached to aluminum stubs. The samples were then sputter coated with 15 nm of Au—Pd using a Cressington 208HR sputter coater operating in argon. An FEI XL30 Environmental Scanning Electron Microscope (ESEM) operating at 10 kV in Hi-Vac mode was used to obtain photomicrographs.

Example 5

FTIR Analysis of Eudragit® L30D-55 and ACAP-Eudragit Coating Layers

Figure 9:
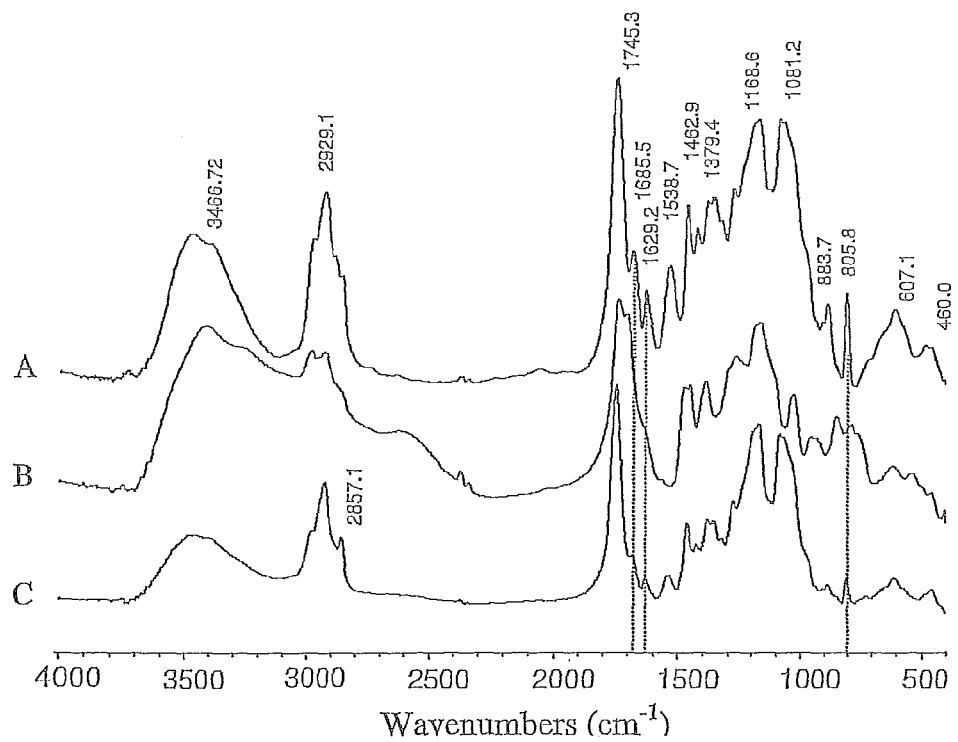
FIG. 9 shows Fourier transform infrared spectroscopy ("FTIR") graphs for various coating formulations, including a coating layer formulated with (acrylamidomethyl)cellulose acetate propionate ("ACAP") (as graph "A"), a coating layer formulated with Eudragit® L30D-55 ("Eud") (as graph "B"), and double-coated layers of ACAP-Eud that were sequentially deposited (as graph "C"), as described in Example 5.

FIG. 9 shows FTIR graphs for various coating formulations, including a coating layer formulated with (acrylamidomethyl)cellulose acetate propionate ("ACAP") (as graph "A"), a coating layer formulated with Eudragit® L30D-55 ("Eud") (as graph "B"), and double-coated layers of ACAP-Eud that were sequentially deposited (as graph "C"). In FIG. 9, the peaks at wave numbers of 3466 $cm^{-1}$ and 2929-3021 $cm^{-1}$ are due to free hydroxyl and intermolecular hydroxyl groups, respectively. The peak at 1745 $cm^{-1}$ is due to ester carbonyls. Other peaks assigned to ACAP: 1685 $cm^{-1}$ (amide group), 1379 $cm^{-1}$ (—C—N— stretching), 1629 and 805 $cm^{-1}$ (C═C stretching). Peaks assigned to Eudragit®: 1160 $cm^{-1}$ (C—CO—C— stretching), 1385 $cm^{-1}$ ($CH_3$— asymmetric bending), 1424 $cm^{-1}$ ($CH_2$— symmetric bending) and 1736 $cm^{-1}$ (C═O stretching). Curve C is a spectrum from the ACAP-Eud coating on alginate hydrogel capsules, and shows the presence of both Eudragit®-specific and ACAP-specific peaks: 1629, 805 $cm^{-1}$ (C═C stretching), 1177 $cm^{-1}$ (C—CO—C— stretching), 1383 $cm^{-1}$ ($CH_3$— asymmetric bending). The shift of C—CO—C— stretching from 1160 $cm^{-1}$ to 1177 $cm^{-1}$ may be indicative of complex formation or hydrogen bonding between ACAP and Eudragit®.

Fourier transform infrared spectroscopy (FTIR) spectra of Eudragit ®, ACAP, and ACAP-Eud coating materials were recorded with a Fourier transform infrared spectrophotometer (Nexus™, 670 FT-IR, Thermo Nicolet) using the KBr disc sampling method. Each sample was gently triturated with KBr powder in a sample-to-KBr weight ratio of 1:100, and then pressed into a disc. The disc was placed in the sample holder and scanned from 4000 to 450 $cm^{-1}$ at a resolution of 4 $cm^{-1}$.

Example 6

DSC Analysis of Eud and ACAP-Eud Coating Layers

Figure 10:
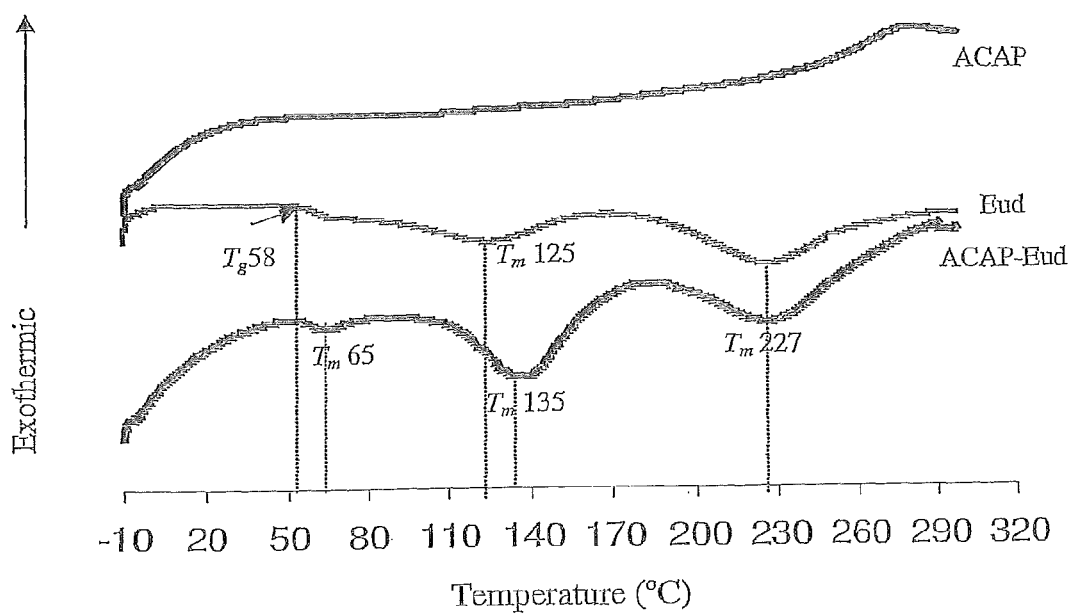
FIG. 10 shows differential scanning calorimetry ("DSC") graphs for various coating formulations, including a coating layer formulated with Eudragit® L30D-55 (as curve "Eud"), a coating layer formulated with (acrylamidomethyl)cellulose acetate propionate (as curve "ACAP'), and double-coated layers of ACAP-Eud that were sequentially deposited (as curve "ACAP-Eud"), as described in Example 6.

FIG. 10 shows DSC graphs for various coating formulations, including a coating layer formulated with Eudragit® L30D-55 (as curve "Eud"), a coating layer formulated with (acrylamidomethyl)cellulose acetate propionate (as curve "ACAP'), and double-coated layers of ACAP-Eud that were sequentially deposited (as curve "ACAP-Eud"). In FIG. 10, DSC curves for the Eudragit® coating layer, the ACAP coating layer, and the ACAP-Eudragit® coating layers were measured at the same heating rate. The Eudragit® curve showed a sharp endothermic melting peak at 227° C. The inclination in the graph between 55° C. and 60° C. is related to the glass transition temperature ($T_g$). The apparent $T_g$ for ° C. at 115° C. reported in the literature was not reproducible in this study, and an additional transition at 125° C. ($T_m$) was observed. Pure ACAP exhibited no apparent $T_g$ or $T_m$ in the range between −10° C. and 290° C. The ACAP-Eud curve exhibited three endothmic peaks at 65° C., 135° C., and 227° C., respectively. These peaks shifted to slightly higher temperatures compared to the $T_m$ of Eudragit®, and suggested the occurrence of possible polymorphic changes after the ACAP coating formation onto the Eudragit® coating layer.

Differential scanning calorimetry (DSC) curves of the dried Eudragit® layer, ACAP layer, and ACAP-Eud layer were respectively recorded using a differential scanning calorimeter (DSC Q100/TGA Q500, TA Instruments). Each sample (2-2.5 mg) was weighed and placed into a 40 μl aluminum pan with an aluminum cover. Measurements were performed over a range from −10° C. to 400° C. at a heating rate of 10° C./min.

Example 7

Water Retention of Coated Alginate Hydrogel Capsules

Figure 11:
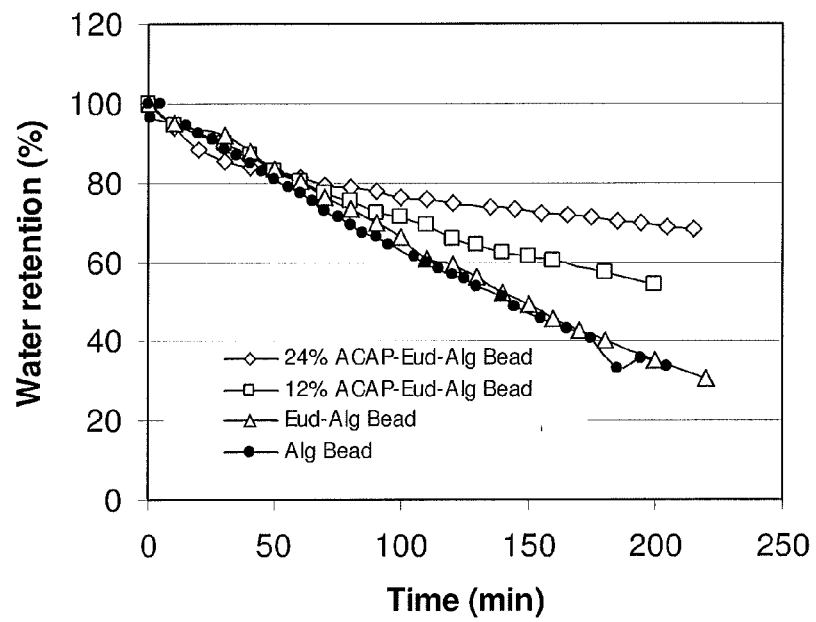
FIG. 11 shows water-retention profiles, expressed as % weight retention, for various hydrogels tested, including alginate hydrogel capsules ("Alg Bead"), Eud-coated alginate hydrogel capsules ("Eud-Alg Bead"), alginate hydrogel capsules coated with 12% ACAP-Eud ("12% ACAP-Eud-Alg Bead"), and alginate hydrogel capsules coated with 24% ACAP-Eud-Alg ("24% ACAP-Eud-Alg Bead") respectively, measured at room conditions of 23° C. and RH 50%, as described in Example 7.

FIG. 11 shows water-retention profiles, expressed as % weight retention, for various hydrogels tested, including alginate hydrogel capsules ("Alg Bead"), Eud-coated alginate hydrogel capsules ("Eud-Alg Bead"), alginate hydrogel capsules coated with 12% ACAP solution ("12% ACAP-Eud-Alg Bead"), and alginate hydrogel capsules coated with 24% ACAP solution ("24% ACAP-Eud-Alg Bead") respectively, measured at room conditions of 23° C. and RH 50%. In FIG. 11, the loss in water content from alginate hydrogel capsules and from Eud-Alg hydrogel capsules occurred linearly with respect to storage time. The percentage of water retention decreased to less than 40% of the initial water content after 200 min. Nevertheless, a significant reduction in water migration was observed in Eud-Alg hydrogel capsules coated with the ACAP coating layer. Water migration was further reduced as the concentration of the ACAP solution was increased from 12% to 24%. For example, the 24% ACAP-Eud-coated alginate hydrogel capsules exhibited 75% water retention after 200 min, as compared to the 12% ACAP-Eud-coated alginate hydrogel capsules that exhibited 55% water retention for the same storage period. Thus, an increase in the ACAP concentration can facilitate the formation of a water-tight layer. Subsequent to complete evaporation of acetone, a solvent-free polymeric coating layer can be formed easily and quickly to prevent further water losses. After exposure for three weeks, the 24% ACAP-Eud-Alg hydrogel capsules demonstrated 29% water retention. It is noted that any decrease in weight percentage due to solvent losses from the various coatings during the drying process were included in the value representing total water loss for simplicity. This is reasonable in that the weight of the hydrogel capsule is substantially due to water molecules impregnated within the alginate matrix. The data supports that the disclosed coating formulations can effectuate a significant reduction in water migration and a significant enhancement in water retention within the coated hydrogel capsules.

The stability of coated alginate hydrogel capsules exposed to room conditions (23° C., 50% RH) is described as percent of water retention. Namely, values were determined as percent of weight retention of the hydrogel capsules by measuring the weight of individual hydrogel capsules at regular time intervals via a gravimetric technique and using the following equation: % of water retention in a hydrogel capsule=$100\% \times [W_{ow} - W_{loss}]/W_{ow}$ (1) in which the $W_{ow}$ is the weight of a newly formed hydrogel capsule (at time zero of the experiment), and the $W_{loss}$ is the weight loss of a hydrogel capsule after a certain period of time. With respect to the ACAP-Eud-Alg hydrogel capsule, any weight loss of solvent (acetone) occurring at room temperature conditions were considered negligible and thus, included as part of the total water losses for simplicity.

Example 8

The Effect of pH in Stabilizing Eudragit®-Coated Alginate Hydrogel Capsules

Figure 12:
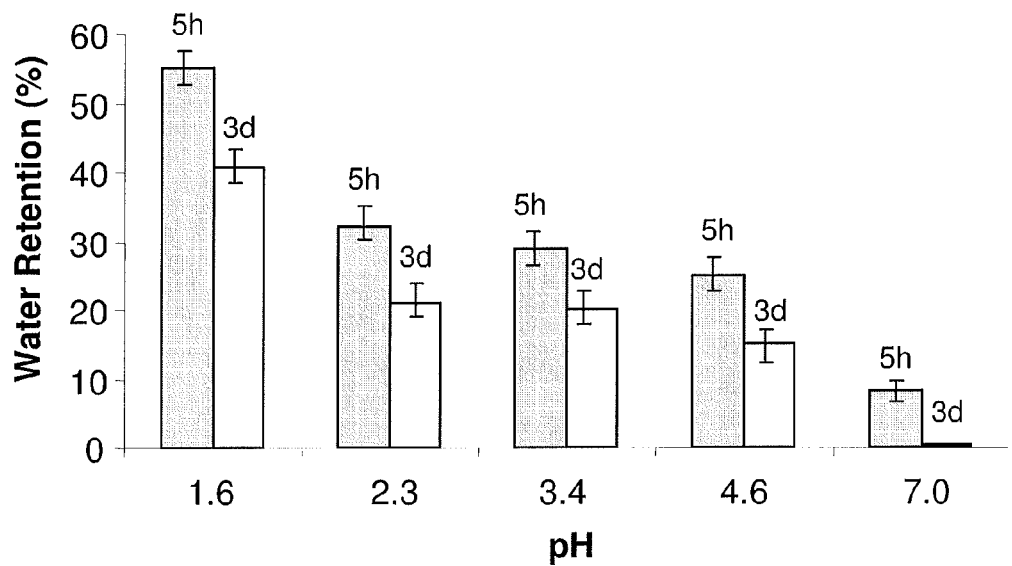
FIG. 12 shows short-term (5 hours) and long-term (3 days) water-retention profiles, expressed as % weight retention, for Eud-coated alginate hydrogel capsules that were exposed to different pH conditions after coating with Eudragit®, measured at 23° C. and RH 50%, as described in Example 8.

FIG. 12 shows short-term (5 hours) and long-term (3 days) water-retention profiles, expressed as % weight retention, for Eud-coated alginate hydrogel capsules that were exposed to different pH conditions after coating with Eudragit®, measured at 23° C. and RH 50%. The pH effect on Eud-Alg hydrogel capsules was tested by immersing hydrogel capsules into buffer solutions at various pH values of 1.6, 2.4, 3.4, 4.6, and 7.0, respectively, at room temperature for 10 seconds. Eudragit® is a pH-dependent, film-forming material that can dissolve in water at pH over 5.5.

The Eud-Alg hydrogel capsules were subsequently immersed in HOAc/NaOAc buffer solutions having pH values ranging from 1.6 to 7.0. Generally, as the buffer solution is increased in pH, the % of water retention by the hydrogel capsules decreases. For example, at the pH of 1.6, the Eud-Alg hydrogel capsules exhibited 40% water retention after three days. In contrast, at the pH of 4.6, the Eud-Alg hydrogel capsules exhibited 18% at a comparable time point. The pH effect on the water retention capacity of Eud-Alg hydrogel capsules can be the result of changes in the degree of ionization for both Eudragit® and alginate under different pH conditions. Since the pKa of the Eudragit® carboxylic group is 2.68, the degree of ionization of Eudragit® can change significantly between pH 2.4 and 7.0. Moreover, the degree of ionization of alginate (pKa around 4) can also change in this pH range. At a low pH, Eudragit® ionization decreases. The non-ionized chains of Eudragit® tend to form a tighter network, which results in reduced water permeability. At a higher pH value, the Eudragit® coating can progressively ionize and undergo swelling so that water permeability increases, resulting in water loss. The data suggests that exposing Eud-Alg hydrogel capsules to low pH conditions can improve their water retention properties.

Figure 13A:
FIG. 13A shows the effect on the surface morphology of Eud-Alg hydrogel capsules exposed to pH 1.6 condition after coating with Eudragit®, as described in Example 8.

FIG. 13A shows the effect on the surface morphology of Eud-Alg hydrogel capsules exposed to pH 1.6 condition after coating with Eudragit®. At pH value of 1.6, the coating layer exhibited tight surface tension resulting in a lower rate of water loss.

Figure 13B:
FIG. 13B shows the effect on the surface morphology of Eud-Alg hydrogel capsules exposed to pH 4.6 condition after coating with Eudragit®, as described in Example 8.

FIG. 13B shows the effect on the surface morphology of Eud-Alg hydrogel capsules exposed to pH 4.6 condition after coating with Eudragit®. At pH value of 4.6, the coating layer appeared to be partially eroded resulting in a higher rate of water loss.

Example 9

Effect of Heat in Stabilizing Eudragit®-Coated Alginate Hydrogel Capsules

Figure 14:
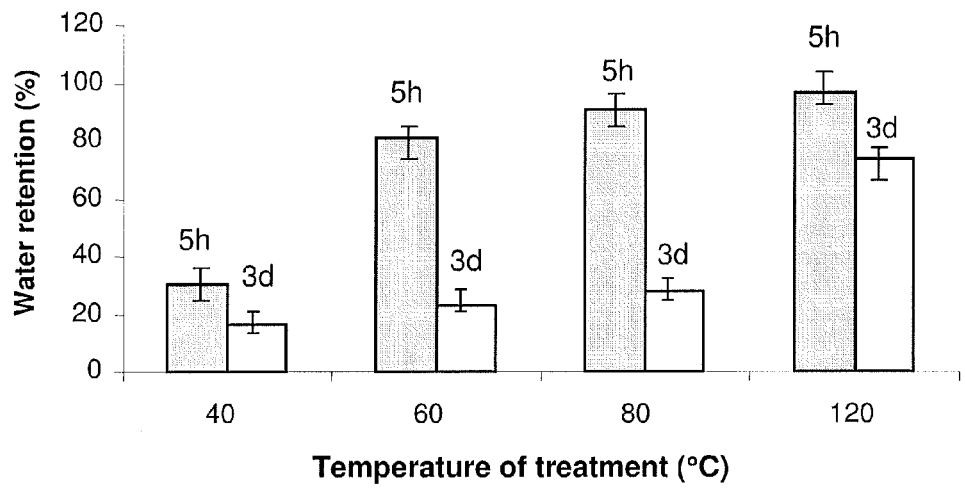
FIG. 14 shows short-term (5 hours) and long-term (3 days) water-retention profiles, expressed as % weight retention, for Eud-coated alginate hydrogel capsules that were exposed to different thermal exposure after coating with Eudragit®, measured at 23° C. and RH 50%, as described in Example 9.

FIG. 14 shows short-term (5 hours) and long-term (3 days) water-retention profiles, expressed as % weight retention, for Eud-coated alginate hydrogel capsules that were exposed to different thermal exposure after coating with Eudragit®, measured at 23° C. and RH 50%. In FIG. 14, higher % water retention within the Eud-Alg hydrogel capsules was observed for capsules treated at higher temperatures. Heat exposure at 120° C. for 5 min was the most effective temperature/duration tested, in that the water retention was 75% after 5 hours of aging, and about 59% after 3 days of aging. In addition, the % water retention of the 24% ACAP-Eud-coated alginate hydrogel capsules after heat exposure at 60° C. for 10 min was 56% after 5 hours, and 51% after 3 days, measured at 23° C. and 50% RH.

Figure 15:
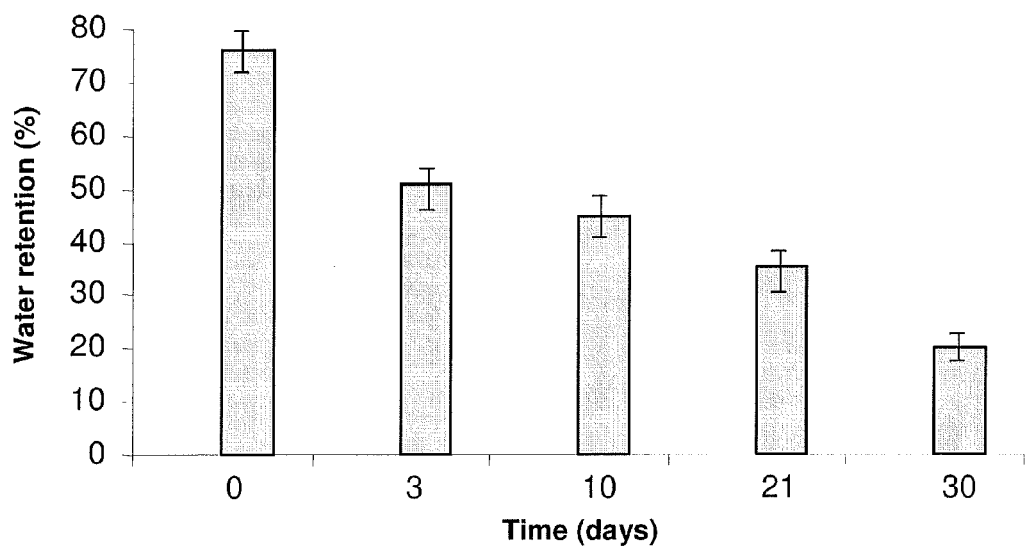
FIG. 15 shows water-retention profiles, expressed as % weight retention, for ACAP-Eud-coated alginate hydrogel capsules that were exposed to 60° C. for 10 min, after coating with Eudragit®, measured at 23° C. and RH 50%, as described in Example 9.

FIG. 15 shows water-retention profiles, expressed as % weight retention, for ACAP-Eud-coated alginate hydrogel capsules that were exposed to 60° C. for 10 min, after coating with Eudragit®, measured at 23° C. and RH 50%. The % water retention decreased to 35% after 3 weeks of exposure at room conditions.

Table 1 below shows the effect of heat exposure on water retention properties, expressed as % water loss by weight, for Eudragit® coating formulations deposited on the surface of alginate hydrogel capsules. The percentage of water retained in the various Eud-Alg hydrogel capsules after heat exposure ranged from ~79 to ~84%. In particular, the exposure of Eud-Alg hydrogel capsules to 40° C. for 10 min can reduce the weights of the hydrogel capsule by about 13%. Exposure of the Eud-Alg hydrogel capsules to 60° C. or 80° C. for 10 min, can reduce the weights of the hydrogel capsules by about 27% and 33% of, respectively. Exposure of the Eud-Alg hydrogel capsules to 120° C. for 5 min can reduce the weight of the capsules by about 32.5%. The 24% ACAP-Eud-Alg hydrogel capsules exhibited the lowest weight loss after heat exposure at 60° C. for 10 min.

In Table 1, "original water content (%)" is [(wet weight–final dry weight)/wet weight]×100%, and "% water in heat-exposed hydrogel capsule" is [original weight of hydrogel capsule ×original water %–weight loss of heat-exposed hydrogel capsule]/[original weight of hydrogel capsule–weight loss of heat-exposed hydrogel capsule]×100%.

TABLE 1

| Beads | Original Water Content (%) | Temp (° C.) | Time (min) | Water Loss after heat exposure (wt. %) | % Water post-heat exposure (wt. %) |
|---|---|---|---|---|---|
| Eud-Alg | 86 ± 1 | 40 | 10 | 13.6 ± 3 | 84 ± 3 |
| Eud-Alg | 86 ± 1 | 60 | 10 | 27.6 ± 3 | 81 ± 3 |
| Eud-Alg | 86 ± 1 | 80 | 10 | 32.9 ± 3 | 79 ± 3 |
| Eud-Alg | 86 ± 1 | 120 | 5 | 32.5 ± 3 | 79 ± 3 |
| 24% ACAP-Eud-Alg | 78 ± 1 | 60 | 10 | 8.3 ± 3 | 76 ± 3 |

The thermal effect may be attributed to increased mobility of the polymer chains at higher temperatures and to improved consolidation by the inter-diffusion of polymer chains as Eudragit® particles aggregate within the coating layer, driven by capillary action that promotes water evaporation during thermal exposure. Efficient coating/film formation and efficient coalescence of dispersed latexes can generally be achieved at temperatures above the $T_g$ of the latex polymer of Eudragit®. Based on DSC analysis, phase transitions of Eudragit® were observed at 58° C. and 125° C. When Eud-coated alginate hydrogel capsules were exposed to 120° C., which is a higher value than the reported $T_g$ value (115° C.), the Eudragit® copolymer can assume a more flexible rubbery state that can contribute to a more suitable coating/film. Exposing Eud-coated alginate hydrogel capsules to 120° C. for 5 minutes can induce stress relaxation and promote the orientation of the Eudragit® copolymer to alter the coating layer morphology conducive in preventing water diffusion through the Eudragit® coating.

Figure 16A:
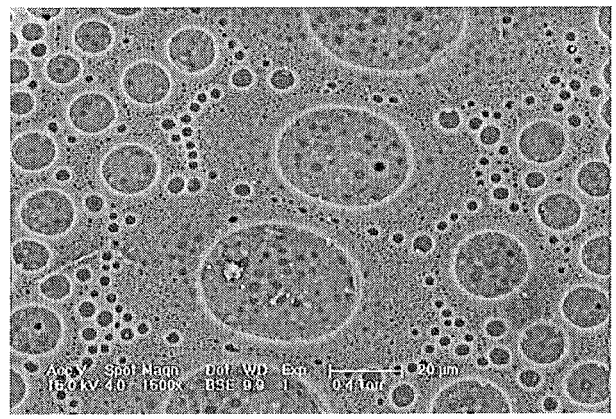
FIG. 16A shows the surface morphology of ACAP-Eud-Alg hydrogel capsules not exposed to heat, as described in Example 9.

FIG. 16A shows the surface morphology of ACAP-Eud-Alg hydrogel capsules not exposed to heat. In FIG. 17A, an array of circular indentations, or pits were observed on the surface. Larger indentations were usually arranged along a linear pathway, and were surrounded by smaller pits that were about 20 μm in pore size.

Figure 16B:
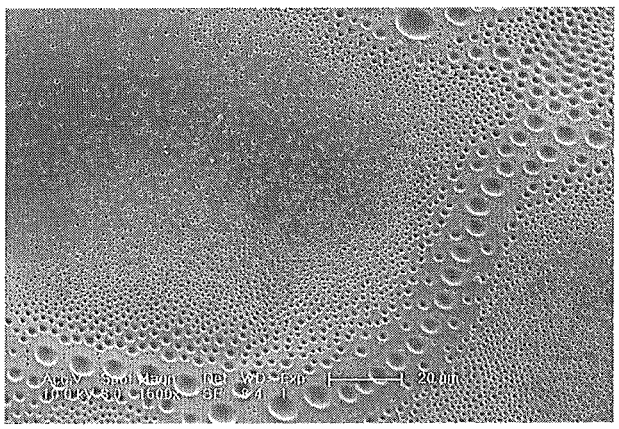
FIG. 16B shows the surface morphology of ACAP-Eud-Alg hydrogel capsules exposed to 60° C. for 10 min, as described in Example 9.

FIG. 16B shows the surface morphology of ACAP-Eud-Alg hydrogel capsules exposed to 60° C. for 10 min. In FIG. 17B, some significant morphological changes were observed on the surface of hydrogel capsules subjected to heat exposure. A large number of randomly shaped depressions were observed on the surface after 60° C. treatment for 10 min. Large depressions were concentrated on the peaks, but as the valleys were approached, the depressions decreased in size, and were spread over a larger surface area. These depressions were not pores.

The effect of heat on Eud-coated alginate hydrogel capsules or ACAP-Eud-coated alginate hydrogel capsules was tested as follows: 1) placing the Eud-Alg hydrogel capsules in an oven at 40, 60 or 80° C., respectively, for 10 min; 2) placing the Eud-Alg hydrogel capsules in an oven at 120° C. for 5 min; and 3) placing the ACAP-Eud-Alg hydrogel capsules in an oven at 60° C. for 10 min. Eudragit® has a reported glass transition temperature ($T_g$) of 115° C. Above $T_g$, the mobility of the polymer chain increases, and may significantly impact the permeability of Eudragit® coating. The length of time for each heat exposure was optimized to minimize the water evaporation during the evaluation process.

Example 10

Effect of Heat in Stabilizing Eudragit®-Coated Alginate Hydrogel Capsules

Figure 17:
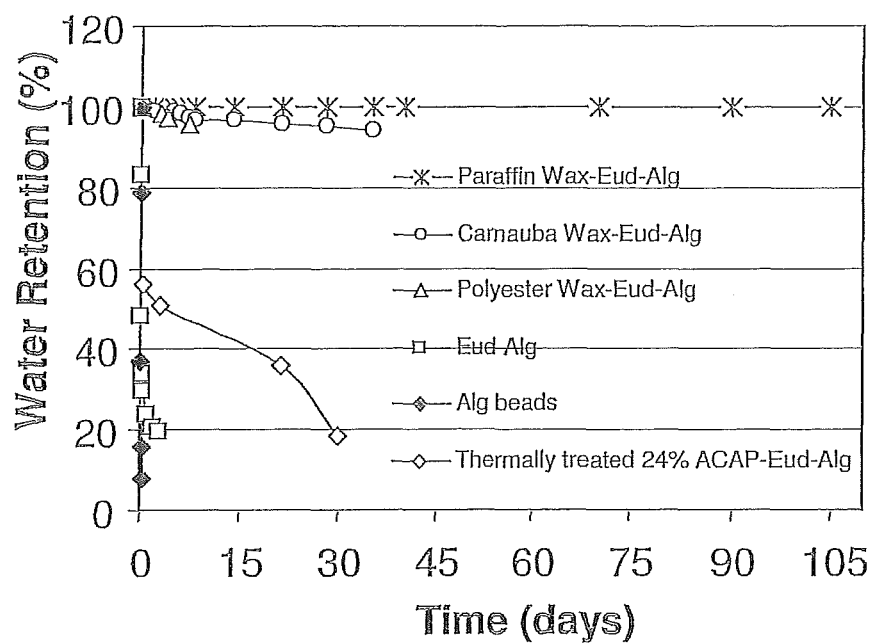
FIG. 17 shows water-retention profiles, expressed as % weight retention, for various combinations of coating formulations deposited on the surface of alginate hydrogel capsules, measured at room conditions 23° C. and RH 50%, as described in Example 10.

FIG. 17 shows water-retention profiles, expressed as % weight retention, for various combinations of coating formulations deposited on the surface of alginate hydrogel capsules, measured at room conditions 23° C. and RH 50%. In FIG. 17, the Eud-Alg hydrogel capsules not subjected to pH or heat treated could not effectively inhibit the evaporation of water from the alginate gel matrix when compared to uncoated alginate hydrogel capsules (negative control). The 24% ACAP-Eud-coated hydrogel capsules that were exposed to heat demonstrated improved water retention properties with aging, but only moderately.

Table 2 below provides % weight retention measured for various combinations of coating formulations plotted in FIG. 18. "Open" samples were stored in open trays at room condition 74° F. and 50% RH. "Close" samples were stored at room condition 74° F. and 50% RH in 32 ml vials with snap caps.

TABLE 2

| | Water Retention (%) with Storage at 74° F. (23° C.) and 50% RH | | | | | | | | | |
|---|---|---|---|---|---|---|---|---|---|---|
| | 1 week | | 2 weeks | | 3 weeks | | 4 weeks | | 5 weeks | |
| Bead Type | Open | Close | Open | Close | Open | Close | Open | Close | Open | Close |
| Alginate alone | 0 | 87 | 0 | 74.3 | 0 | 66.6 | 0 | 53.4 | 0 | 21.7 |
| Eud-coated | 0 | 91.6 | 0 | 81.5 | 0 | 74.1 | 0 | 61.3 | 0 | 57.5 |
| Polyesterwax-Eud | 95.6 | — | — | — | — | — | — | — | — | — |
| Carnaubawax-Eud | 97.6 | — | 96.5 | — | 95.6 | — | 94.8 | — | 93.9 | — |
| Paraffinwax-Eud | 100 | — | 100 | — | 100 | — | 100 | — | 100 | — |

TABLE 2-continued

| | Water Retention (%) with Storage at 74° F. (23° C.) and 50% RH | | | | | | | | | |
|---|---|---|---|---|---|---|---|---|---|---|
| | 7 weeks | | 9 weeks | | 11 weeks | | 13 weeks | | 15 weeks | |
| Bead Type | Open | Close | Open | Close | Open | Close | Open | Close | Open | Close |
| Alginate alone | 0 | — | 0 | — | 0 | — | 0 | — | 0 | — |
| Eud-coated | 0 | — | 0 | — | 0 | — | 0 | — | 0 | — |
| Polyesterwax-Eud | — | — | — | — | — | — | — | — | — | — |
| Carnaubawax-Eud | — | — | — | — | — | — | — | — | — | — |
| Paraffinwax-Eud | 100 | — | 100 | — | 100 | — | 100 | — | 100 | — |

The wax coatings significantly improved the percent water retention. The type of wax selected can make a significant contribution to the effectiveness of the coating in preventing water loss. Polyester-wax-coated hydrogel capsules exhibited 95.6% water retention after one week of aging. In contrast, carnauba-wax-coated hydrogel capsules exhibited 97.6% water retention after the same time period. Paraffin wax, however, formed the most effective water-impermeable coating layer, as the Paraffin Wax-Eud-coated alginate hydrogel capsules demonstrated almost 100% water retention when left in an open tray at 23° C. and 50% RH for fifteen weeks (three months). Wax is highly hydrophobic and contains large content of long-chain alkanes. A coating layer comprising a wax formulation can be effective in forming a low-permeability coating layer that can be deposited onto the surface of hydrogel capsules containing a substantial amount of water. Any natural polymer can be employed for producing the hydrogel matrix, such as alginate, to serve as a carrier of water, water-soluble flavors, or water-soluble active agent of interest. The hydrogels enveloped by the disclosed coating formulations exhibit desirable properties, including mechanical strength and low-permeability. Unlike the film-coating processes described herein for the formation of latex-like/polymer coatings, the dip-wax coating process does not require the use of solvents that may lead to environmental problems, solvent residues, or excessive recovery costs.

It will be appreciated that, although specific embodiments of the invention have been described herein for purposes of illustration, various modifications may be made without departing from the spirit and the scope of the invention. Accordingly, the invention is not limited except as by the appended claims. Unless defined otherwise, all technical and scientific terms have standard meaning as commonly understood to persons skilled in the art. Although exemplary methods, devices, and materials have been described with particularity, alternative methods and materials, that may be similar or equivalent to those described herein, are applicable for making the disclosed compositions and for practicing the disclosed methods.

What is claimed is:

1. A capsule comprising:
    a core comprising gelled alginate and one or more optional additives and having a diameter of 1 to 5 mm,
    a polymeric coating substantially surrounding the core, and
    an optional second coating,
    wherein the capsule exhibits water retention of at least 40% after three days at 23 degrees C. and 50% relative humidity, and
    wherein the polymeric coating comprises (acrylamidomethyl)cellulose acetate propionate.

2. A smoking article or smokeless tobacco product incorporating one or more capsules according to claim 1.

3. The product according to claim 2, wherein the product is a smokeless tobacco product and the smokeless tobacco is contained in a porous wrapper.

4. An orally consumable tobacco-free product incorporating one or more capsules according to claim 1.

5. The product according to claim 2, wherein the product is a cigarette, and the one or more capsules is incorporated in a tobacco rod and/or a filter of the cigarette.

6. The product according to claim 2, wherein the product is moist smokeless tobacco.

7. The capsule according to claim 1, comprising an additive selected from the group consisting of flavorants, tobacco, antioxidants, medicaments, nutraceuticals, cell culture medium, cosmetics, agrochemicals, disinfectants, detergents, and dyestuff.

8. The capsule according to claim 1, comprising a second coating of paraffin wax, carnauba wax or polyester wax.

* * * * *